(12) United States Patent
Pagnacco et al.

(10) Patent No.: US 6,461,297 B1
(45) Date of Patent: Oct. 8, 2002

(54) APPARATUS AND METHODS FOR MEASURING PHYSICAL DISORDERS

(76) Inventors: Guido Pagnacco, 18002 Richmond Place Dr. #827, Tampa, FL (US) 33657; Elena Oggero, 18002 Richmond Place Dr. #827, Tampa, FL (US) 33657; A. Bob Henderson, 10240 Waterside Oaks Dr., Tampa, FL (US) 33647-3193

( * ) Notice: Subject to any disclaimer, the term of this patent is extended or adjusted under 35 U.S.C. 154(b) by 0 days.

(21) Appl. No.: 09/785,612

(22) Filed: Feb. 16, 2001

(51) Int. Cl.[7] .............................................. A61B 19/00
(52) U.S. Cl. ...................................... 600/300; 600/558
(58) Field of Search ................................ 600/300, 558, 600/559, 587

(56) References Cited

U.S. PATENT DOCUMENTS

| | | | | |
|---|---|---|---|---|
| 5,810,747 A | * | 9/1998 | Brundy et al. | 600/300 |
| 5,902,234 A | * | 5/1999 | Webb | 600/300 |
| 6,093,146 A | * | 7/2000 | Filangeri | 600/300 |
| 6,186,145 B1 | * | 2/2001 | Brown | 600/300 |

* cited by examiner

Primary Examiner—Max Hindenburg
(74) Attorney, Agent, or Firm—Parsons & Goltry; Michael W. Goltry; Robert A. Parsons

(57) ABSTRACT

A system comprising a central client, a local client having apparatus for providing therapeutic stimuli and for collecting patient reaction data in response thereto, and a data structure accessible by the local client for storing the reaction data and by the central client for accessing and interacting with the reaction data.

20 Claims, 4 Drawing Sheets

APPARATUS AND METHODS FOR MEASURING PHYSICAL DISORDERS

FIELD OF THE INVENTION

This invention relates to medical and diagnostic devices and, more particularly, to apparatus and methods for measuring biological functions and physical disorders in humans.

BACKGROUND OF THE INVENTION

Nearly one quarter of all fall prevention, dizziness and balance disorder patients suffer from a peripheral vestibular disorder called benign paroxysmal positional vertigo (BPPV), which is treatable with "repositioning therapy." A far greater percentage of balance disorder patients have central problems, or both central and peripheral problems. Central vestibular disorders usually affect the vestibular nerve, the brain stem or the brain and require longer, more-indepth treatments. Presbyastasis, which is an age-related loss of vestibular function, is often the cause of central vestibular disorders in the majority of elderly patients. Other patients can acquire central vestibular disorders as a secondary pathology caused from a primary event or condition such as a stroke, vascular disease, toxicity, a neuromuscular disorder, an auto-immune disease, an inflammatory response, Parkinson's disease or a head injury. Treatment of vestibular disorders that occur as a result of any of these primary events or conditions normally involves extensive physical therapy to bring about either resolution of the primary pathology or central compensation and substitution for the patient. Most patients with vestibular disorders require approximately seven to ten hours of physical therapy, but medical necessity often mandates more prolonged care.

Most patients that have vestibular disorders are first seen by a primary care physician, who evaluates the patient's medical history and examines the patient. If the physician determines that the patient is a candidate for vestibular disorder therapy, the patient is referred to a specialist who also evaluates the patient and prescribes an appropriate treatment regimen.

Typical treatment regimens include a home-based, self-directed therapy component, which involves exercises that patients are to perform several times each day in regimens lasting over a week to ten days, after which the patient returns for another evaluation. The home-based exercises usually involve eye and head movements and other exercises that are designed to improve motor skills, posture and overall balance. If patients do their home-based exercises, they normally enjoy at least some measure of improvement, which allows them to progress into more advanced forms of exercise. The results of the home-based exercise and the gradual progression through increasingly advanced exercise regimens provide patients with cumulative physical benefits, with the goal being to provide the patient with substantially curative or maximum compensation. During this home-based process, which usually lasts two to three months, patients must periodically visit their specialist for progress evaluations.

Patients who diligently prosecute their customized or individualized home-based exercises achieve curative or maximum compensation more efficiently and faster than those who fail to do their prescribed exercises. Historically, studies have shown that patients neglect their exercises because of lack of motivation, because they find the exercises boring and unpleasant or because they either forget how to do them or that they do them incorrectly. Because patients are not monitored on a regular or daily basis throughout their periods of home-based exercise, specialists and therapists and physicians have no way of knowing whether their patients are prosecuting their exercises until the patients return for follow-up evaluations. As a result, many patients who are prescribed home-based exercises do not improve at acceptable rates of progression, which virtually always leads to more prolonged and expensive treatment. For most vestibular disorder patients, current home-based therapeutic regimens are, therefore, inefficient, inadequate and expensive.

Thus, there is a need for improved apparatus and methods for providing and managing therapeutic and evaluative treatment to vestibular disorder patients and to others that utilizes an interactive computer network and associated networked therapeutic components, which allow therapists, specialists, physicians and patients to interact on a regular and ongoing basis throughout periods of home-based therapeutic and evaluative regimens.

SUMMARY OF THE INVENTION

The above problems and others are at least partially solved and the above purposes and others realized in new and improved apparatus, systems and methods for treating and evaluating physical disorders or conditions, for recording measurable responses to at least one of audible and visual stimuli and commands and instructions, and for prosecuting treatment, therapeutic and evaluative regimens over a networked computer environment. In a preferred embodiment, the invention is comprised of a networked computer architecture that includes a potentially vast number of networked central and local clients. Each local client is equipped with apparatus for providing stimuli and for collecting reaction data in response thereto. The stimuli are designed to elicit patient responses such as head and eye movements and other measurable patient functions or movements that provide information about physical conditions and disorders. The reaction data are expressed as sensible indicia of the patient responses, namely, graphs, charts, numbers, figures, characters, etc.

The network includes a data structure that is accessible by local clients for storing reaction data and by central clients for accessing and interacting with the data. The network is implemented over a generalized or localized networked environment, and the data structure is accessible by the central and local clients over a privately- or publicly-accessible site, such as a privately- or publicly-accessible web site in the environment of the Internet. The apparatus is generally comprised of a unit that is adapted and arranged to provide the stimuli and to collect reaction data, and an associated and interactive, computer-implemented software program that is designed to govern therapeutic and evaluative regimens. The apparatus may further include a verbal command structure for facilitating verbal command interaction between the unit and the software program, and an associated microphone for facilitating verbal command interaction with the verbal command structure.

The local clients are for patients and they are remote from the central clients, which are administered by therapists, specialists, physicians or other authorized clinical or medical personnel. Because the central clients can access the stored reaction data, patient progress during the course of home-based therapeutic and evaluative regimens can be monitored and managed at the central clients. Because the invention is implemented in a networked computer environment, therapists, specialists and physicians and other authorized clinical personnel can communicate with patients by way of conventional electronic mail systems and by way of patient electronic documents, which house patient reaction data. In this regard, local clients have access to the data structure for not only storing reaction data into their electronic documents, but also accessing important information periodically provided from their therapists, specialists, doctors and other authorized clinical personnel.

Consistent with the foregoing, the invention also contemplates associated networked architectures and methods for prosecuting and managing therapeutic and evaluative regimens over a networked computer environment.

BRIEF DESCRIPTION OF THE DRAWINGS

Referring to the drawings.

DETAILED DESCRIPTION OF A PREFERRED EMBODIMENT

Figure 1:
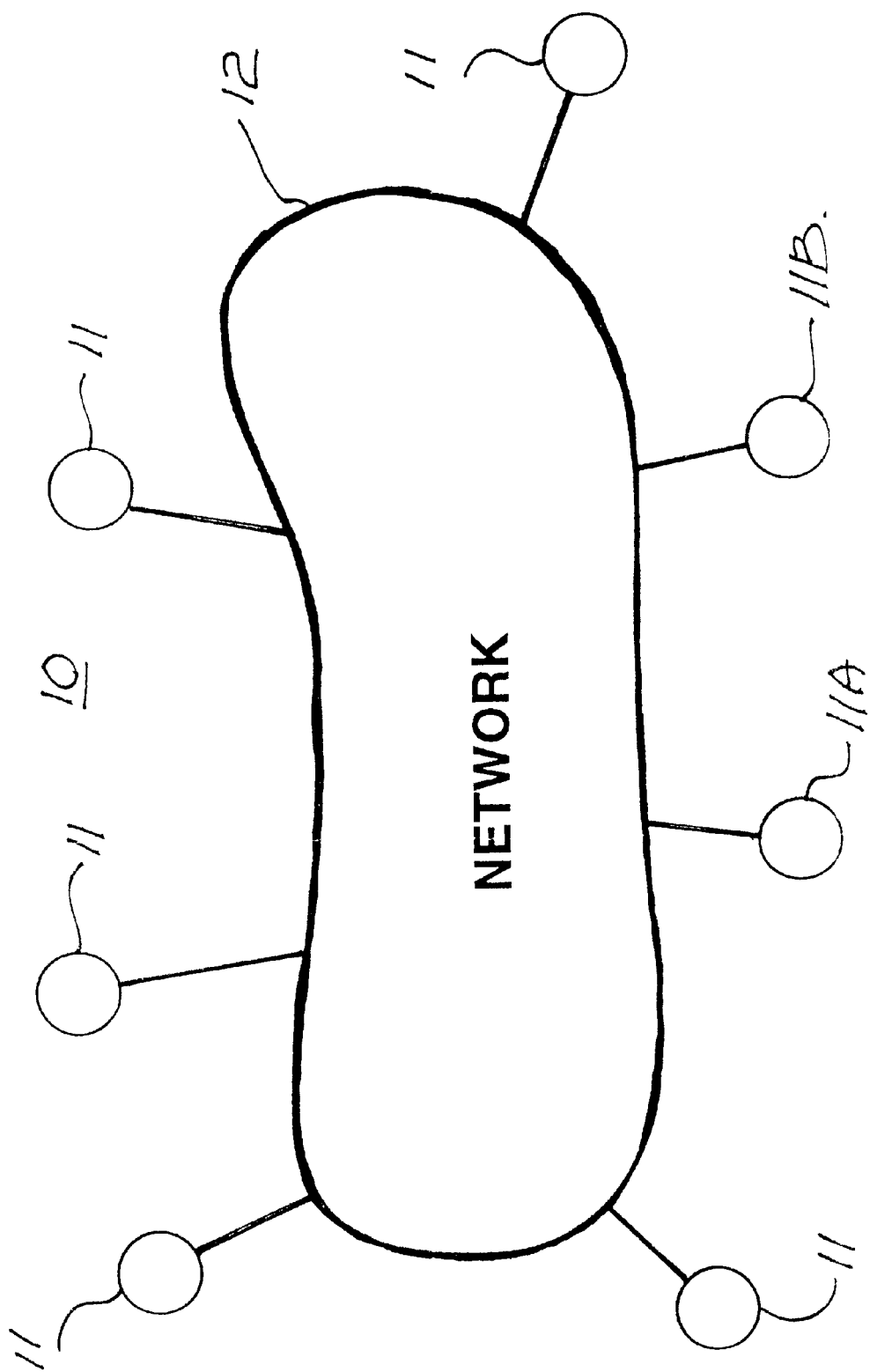
FIG. 1 is a highly schematic diagram of a networked computer environment.

Ensuing embodiments of the invention comprise new and improved apparatus, systems and methods for treating and evaluating physical disorders or conditions, for recording measurable responses to stimuli and for prosecuting and managing therapeutic and evaluative regimens over a networked computer environment. The stimuli comprise at least one of audible and visual stimuli and commands and instructions. Ensuing embodiments of the invention utilize a networked computer environment, and the following discussion deals primarily with the Internet and the world-wide-web. However, those conversant in the art will appreciate that the apparatus and methods set forth in this specification may be implemented in any generalized or localized networked computer environment.

In general, the invention proposes a computer network of a potentially vast number of central and remote local clients. Each of the local clients is equipped with apparatus for providing stimuli as previously and generally defined and for collecting patient responses thereto in the form of reaction data. The stimuli are designed to elicit patient responses. The patient responses, which can be eye and head movements and other bodily functions or movements, are measurable and provide information about physical conditions or disorders. The reaction data are expressed as sensible indicia of the patient responses, namely, graphs, charts, numbers, figures, characters, etc.

The invention includes a data structure, which is accessible by each of the local clients for storing the reaction data and by each of the central clients for accessing and interacting with the reaction data. The data structure is accessible by the central and local clients over a publicly- or privately-accessible web site or by way of a localized computer network, and the invention may incorporate an encryption and password scheme for privacy and confidentiality. The apparatus of each of the local clients is more specifically comprised of a unit that is adapted and arranged to provide the stimuli and to collect reaction data, and an associated and interactive, computer-implemented software program that manages and governs the operation of the unit. The apparatus may further include a verbal command structure for facilitating verbal command interaction between the unit and the software program, and an associated microphone for facilitating verbal command interaction with the verbal command structure.

In the interests of organization and clarity of the ensuing detailed description of the specific features of the invention, §A presents the structural and functional attributes of a networked computer environment, §B presents the structural and functional attributes of a networked client interface, §C presents the structural and function attributes of therapeutic apparatus of the invention, and §D presents associated methods of prosecuting therapeutic and evaluative procedures and the associated advantages the invention.

§A. A Networked Computer Environment

Turning to the drawings, FIG. 1 illustrates a highly schematic diagram of a networked computer environment 10 comprising clients 11 connected together through a network 12. Clients 11 include, among other networked components, displays and personal computers that are configured to interact with network 12. Each personal computer normally includes or is otherwise associated with storage, processing apparatus, an appropriate software architecture, output apparatus such as a monitor or display and input apparatus such as a keyboard, mouse or pointing device, a voice response architecture, etc. Network 12 comprises a generalized or localized computer network or the Internet. Access to network 12 is normally made over telephone lines such as wired and/or wireless commercial information services or other similar communication systems. To ease the ensuing discussion, one of clients 11 is considered a local client and is denoted with the reference character 11A and discussed below in connection therewith, and another one of clients 11 is considered a central client and is denoted with the reference character 11B. In accordance with the invention, client 11B is located at a hospital or a public or private medical or therapeutic treatment clinic or office or other central location, and is operated and managed by one or more authorized medical or therapeutic specialists or clinical personnel. Client 11A is preferably located at a patient's primary or other residence and it can be located elsewhere. Any one of clients 11 can be either a central client or a local client in accordance with the invention. The invention contemplates a potentially vast number of local and central clients.

§B. A Networked Client Interface

Figure 2:
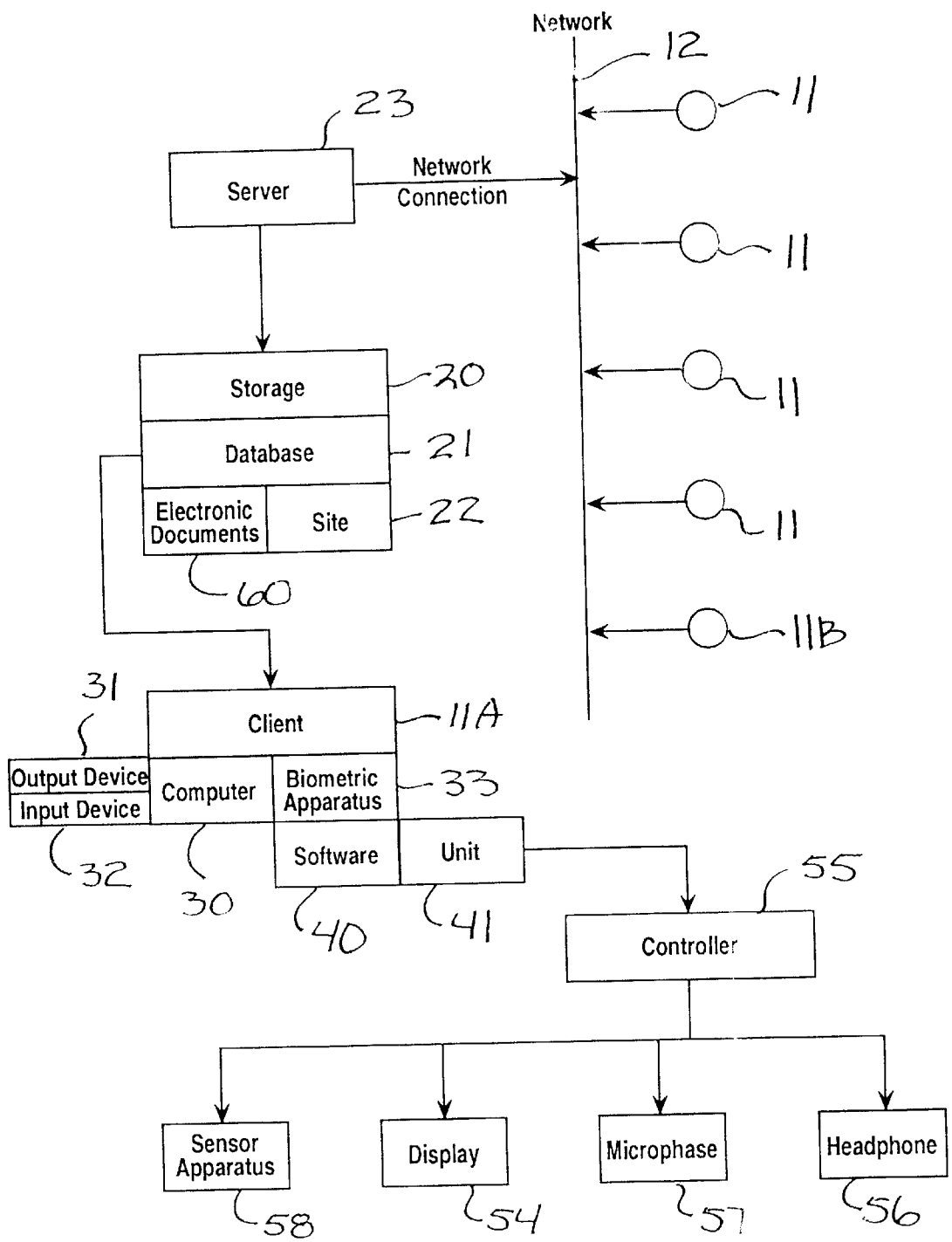
FIG. 2 is a diagram of a networked client interface.
Figure 3:
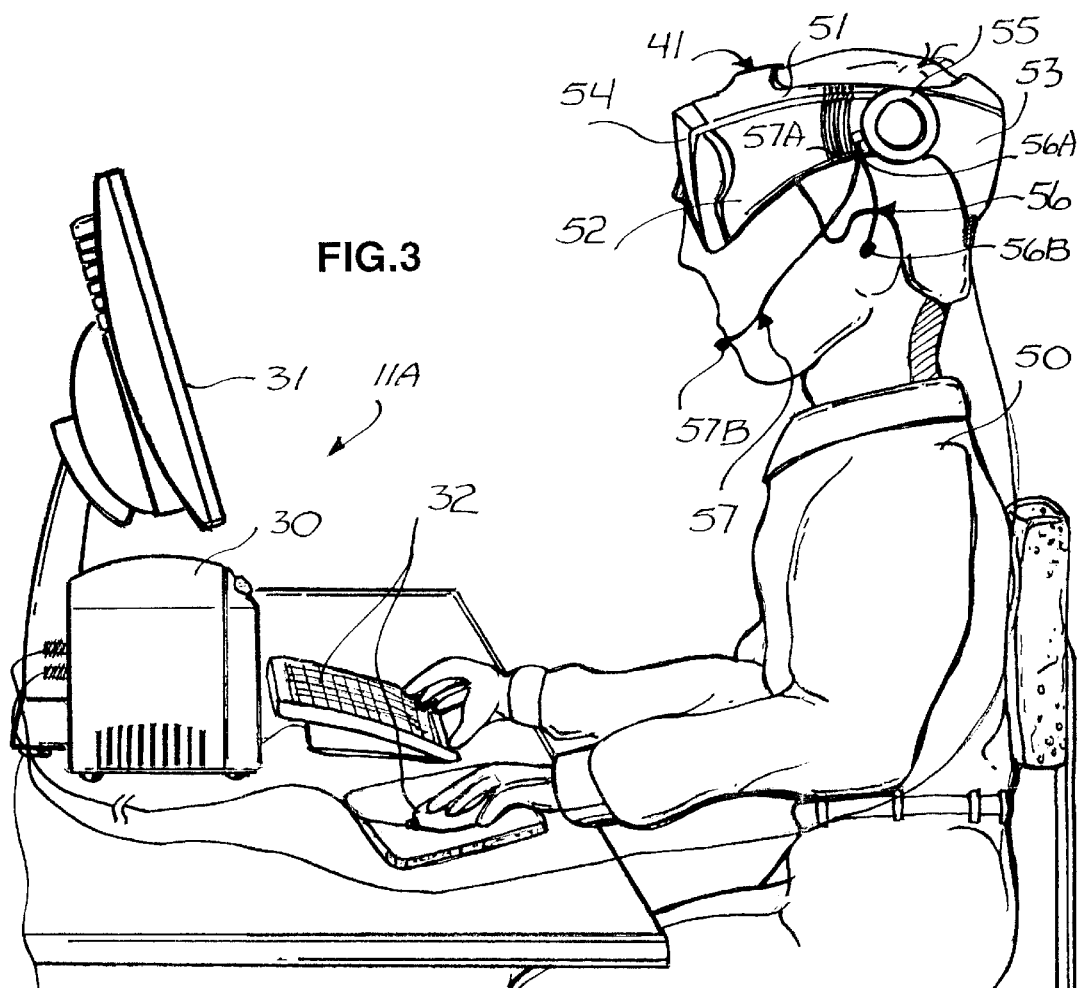
FIG. 3 illustrates a patient interacting with networked components of a networked client, the networked components including a computer having associated input and output apparatus and a unit shown as it would appear worn by the patient, in accordance with the invention.

Looking to FIG. 2 and also to FIG. 3, client 11A includes a computer 30 having an associated output apparatus 31 and preferably a display or monitor, and input apparatus 32 and preferably one or more of a keyboard and pointing device, among potentially other conventional computerized accessories such as a printer, scanner, camera, etc. Regarding FIG. 2, computer 30 includes or is otherwise connected to or associated with storage 20, which houses a database 21. Storage 20 comprises resident and/or central storage and houses software such as a commercially available browser application for facilitating network 12 access and negotiation, and an operating system or platform and preferably one that is multi-tasking and responsive to inputs from client 11A for accessing and interacting with database 21 and with other local and remote networked components. By interacting with network 12, clients 11 can access database 21 by way of a site or portal 22 for conducting document searches and for accessing and interacting with electronic documents. Server 23 facilitates the interface between clients 11 and database 21 in a conventional manner and between client 11A and database 21 in a particular embodiment should storage 20 be totally or at least partially centrally located. Those of ordinary skill will appreciate that the invention may incorporate a potentially vast number of servers for providing a potentially vast number of clients with access to site 22. Should network 12 comprise a local or generalized network, clients 11 may access site 22 with a localized or generalized network application format. Should network 12 comprise the Internet, site 22 may be publicly accessible (i.e., a publicly accessible web site) with a HyperText Transfer Protocol request from any client with a commercially available web browser or, perhaps, within an encrypted virtual private network. Client 11B is also denoted in FIG. 2, and includes substantially the same elements as client 11A, and the other clients 11 can be either local or central clients.

The invention is concerned with treating and evaluating physical disorders or conditions such as dizziness and balance disorders, and it may also be implemented for evaluating other physical conditions such as sight and visual acuity and hearing. Client 11A, like all local clients, is equipped with apparatus 33 for providing stimuli and for recording and storing patient responses to the stimuli. In a preferred embodiment, the operation of apparatus 33 is managed and controlled by computer 30 and, more particularly, by user interaction with computer 30.

§C. Therapeutic Apparatus

Apparatus 33 is generally comprised of software 40 and a unit 41. Software 40 is stored within storage 20 or elsewhere and even at unit 41, is executed by computer 30, by unit 41 or in conjunction with unit 41, and controls the functioning and operation of unit 41. In other words, unit 41 works in conjunction with software 40. Unit 41 is linked to computer 30 over a wired or wireless communication pathway, such as a radio frequency pathway, etc., and preferably the former with conventional or appropriate electrical plug couplings.

Figure 4:
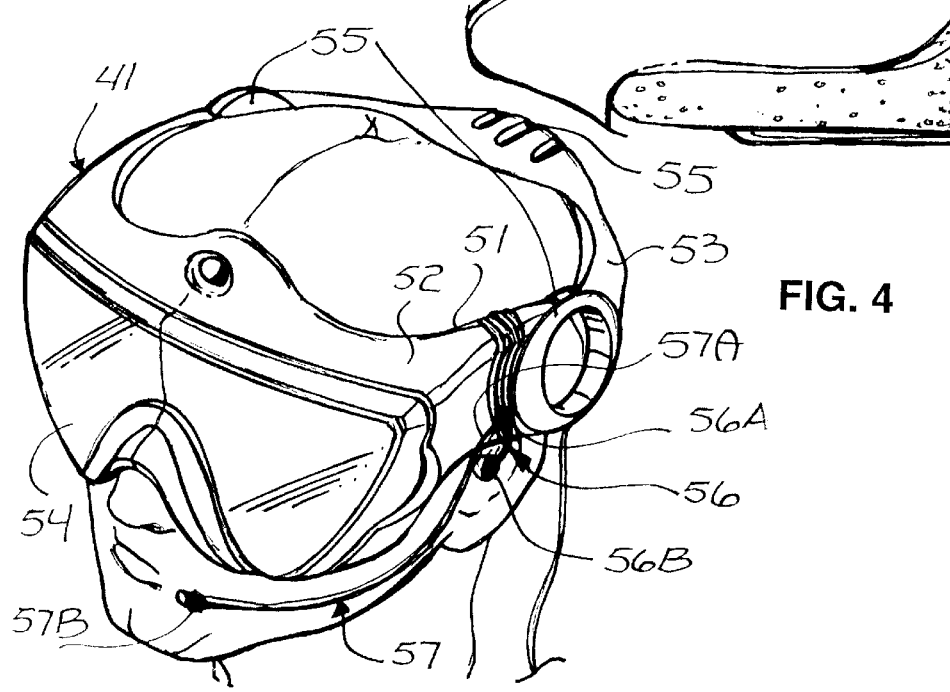
FIG. 4 is a perspective view of the unit of FIG. 3 shown as it would appear being worn by a patient.
Figure 5:
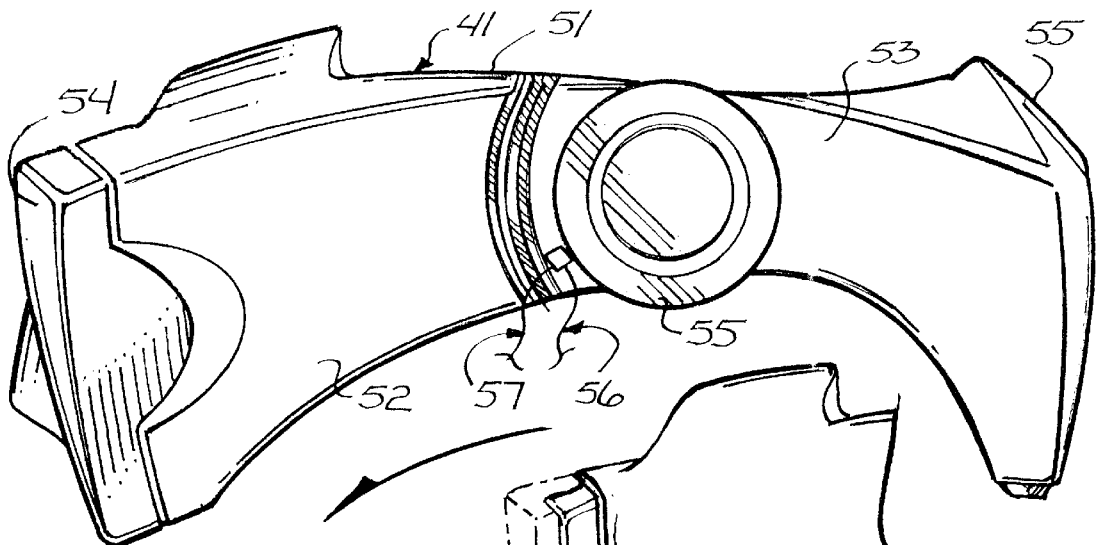
FIG. 5 is a side elevational view of the unit of FIG. 3.

Turning to FIGS. 3 and 4, unit 41 is configured to be worn by the head of a patient 50, and is equipped with features for providing stimuli to the patient, whether audible or visual stimuli and preferably both. The stimuli are governed by the needs of the patient and is provided by software 40, which is preferably interactive and multitasking. Software 40 can be written or modified to address the needs of each individual patient and to otherwise provide each individual patient with unique therapeutic and/or evaluative regimens. As an alternative, the patient may be provided with specific instructions for how to interact with software 40 in accordance with a prescribed therapeutic and/or evaluative regimen.

Looking to FIG. 4, unit 41 is comprised of a housing 51, which is the underlying support for the various components of unit 41. In this specific embodiment, housing 51 is generally circular and is configured to sit atop and substantially encircle the head of the wearer as shown. Housing 51 has forward and rearward portions 52 and 53, and a display 54 is carried by forward portion 52. When properly worn, forward portion 52 is located toward the face of the wearer with display 54 positioned opposite the eyes of the wearer, and rearward portion 53 is located toward the back of the wearer's head. A hinge 55 connects forward portion 52 to rearward portion 53, which allows forward and rearward portions 52 and 53 to pivot and move relative to one another for allowing unit 41 to be worn comfortably by heads of substantially any shape and size. Those skilled in the art will readily appreciate that unit 41 may be configured with other shapes or forms and of substantially any size suitable for comfortably resting upon or engaging the head of a wearer.

Figure 6:
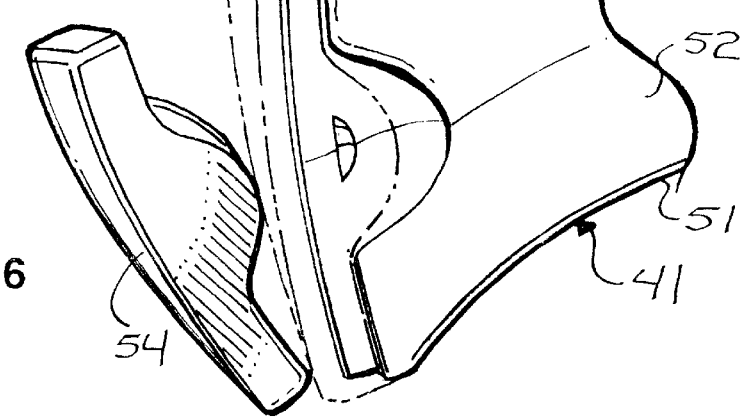
FIG. 6 is a fragmented perspective view of the unit of FIG. 3, with portions thereof broken away for the purpose of illustration.
Figure 7:
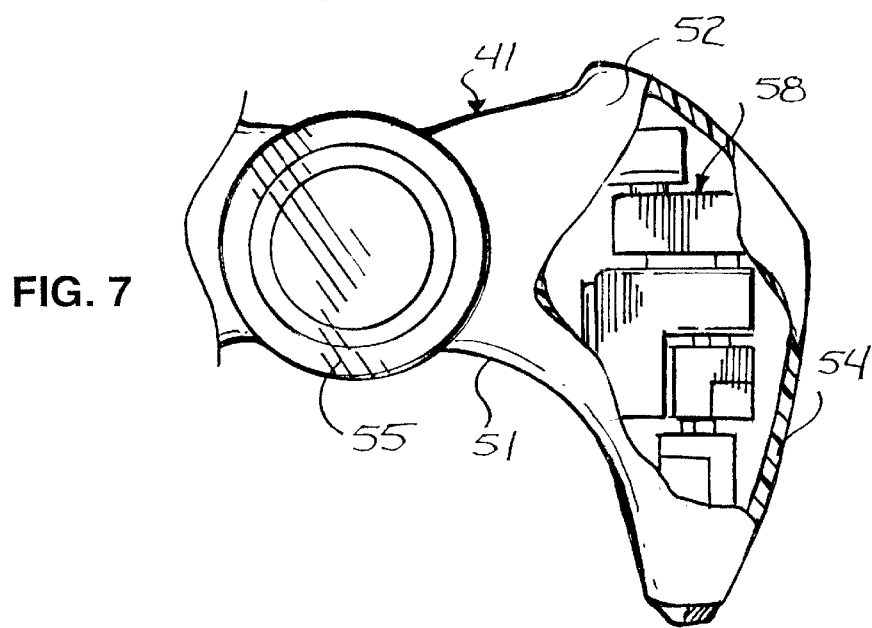
FIG. 7 is a fragmented side view of the unit of FIG. 3, with portions thereof broken away illustrating sensor apparatus of the invention.

In addition to display 54, unit 41 is equipped with a headphone 56 and a microphone 57 as shown in FIGS. 3 and 4, and sensor apparatus 58 as shown in FIG. 6, all of which are channeled through a controller 55. Controller 55 is conventional in structure and design and simply manages the operation of unit 41 and the interaction of unit 41 with computer 30. Unit 41 may be equipped with its own dedicated power source (such as a nickel-cadmium battery or other suitable rechargeable or non-rechargeable power source) for empowering its various components, or it may be provided with electrical power by way of computer 30 or by way of a fixed power source with the use of a power cord. A dedicated power source may be mounted to or otherwise situated anywhere along substantially the entire extent of housing 51, and it may even comprise a discrete component connectable to unit 41 with a power cord. Display 54 is a conventional liquid crystal or reflective display or other suitable display form of a type suitable for use in connection with videonystagmography testing. Display 54 is configured to provide visual stimuli, which preferably comprise moving and/or alternating or flashing targets as governed by software 40 and that a patient is to follow with his or her eyes.

Headphone 56 and microphone 57 are supported by housing 51 and are operatively coupled to controller 55 and are each elongate and include proximal ends 56A and 57A, respectively, attached to housing 51. Headphone 56 includes a free end 56B having a speaker for emitting audible sound, and microphone 57 includes a free end 57B that is adapted and arranged to collect audible sound as with a conventional microphone, as for allowing a user to interact with a computerized voice response architecture implemented by computer 30. Headphone 56 and microphone 57, in conjunction with controller 55, may also be configured and arranged to function as a speakerphone capable of telephonic communication over wired and/or wireless telecommunication pathways. Headphone 56 is flexible, which allows it to be manipulated for locating free end 56B adjacent the exterior acoustic meatus of one of the wearer's ears as substantially shown. Although only one headphone is shown, another one may be provided on the opposite side of housing 51 for the wearer's other ear. Microphone 57 is also flexible, which allows it to be manipulated for locating free end 57B adjacent the wearer's mouth substantially as shown.

Sensor apparatus 58 is adapted and arranged to monitor eye and head movements much like that of conventional videonystagmography goggles, and the stimuli provided to the patient by unit 41 govern the manner in which a patient is directed to move his eyes and head. In this regard, sensor apparatus 58 is configured with one or more cameras and motion sensors for recording and sensing eye and head movements in response to stimuli and for converting such responses into reaction data, which are stored into an electronic document 60, in accordance with the invention. As reaction data are collected by sensor apparatus 58, software 40 is configured to store it into electronic document 60, or to store it first in temporary, resident or central storage and then subsequently and permanently into electronic document 60. Electronic document 60 is contained within database 21, is considered part of the invention, and is created at client 11A or at client 11B. Electronic document 60 is not only accessible by client 11A, but also by client 11B. Because the invention contemplates a potentially vast number of local client, it therefore contemplates a potentially vast number of electronic documents. For security and organizational purposes, access to each electronic document, whether at a client 11A or a client 11B, is preferably managed by an encrypted password scheme, and this may be carried out in any one of a variety of manners in accordance with the art.

§D. Therapeutic and Evaluative Procedures

As previously mentioned, the invention is concerned with treating and evaluating physical disorders or conditions, for recording responses to stimuli and storing the responses in the form of reaction data, and for prosecuting and managing therapeutic and evaluative regimens over a networked computer environment. In accordance with the invention, any patient requiring therapeutic and/or evaluative care for dizziness or for a balance disorder is first evaluated by a medical doctor, therapist, specialist or the like. This evaluation is for the purpose of determining what type, if any, of ongoing therapeutic and/or evaluative care that the patient will need in connection with his or her dizziness or balance disorder. After the required care is established, the invention facilitates its prosecution and management at and between clients 11A and 11B. The required care for dizziness and balance disorders comprises one or more eye and head movement exercises and whole body exercises that are designed to provide therapeutic and/or evaluative results. The nature of the eye and head movement exercises is governed by the stimuli provided to the patient.

In accordance with the invention, the required care is reduced to a therapeutic and/or evaluative curriculum, which may be given directly to the patient in the form of a handout or instruction pamphlet, or in the form of software, such as software 40 or other software. This software may be a) given directly to the patient on a disk, which the patient will later download and access and follow at client 11A, or b) uploaded into electronic document 60 at client 11B, which the patient will later access at client 11A over network 12. In this vein, software 40 can be custom programmed for each specific patient and for his or her specific therapeutic and/or evaluative needs or requirements. As an alternative, the patient may be provided with instructions specific to him or her on how to interact with software 40 in accordance with a prescribed therapeutic and/or evaluative regimen.

In a typical scenario, patient 50 presents himself at client 11A as shown generally in FIG. 3, properly positions unit 41 atop his head as previously explained in §C, and actuates computer 30 and its various components and unit 41 and software 40. Unit 41 may be adapted and arranged to be actuated only by computer 30 and/or independently of computer 30. By interacting with software 40 in accordance with a prescribed curriculum, unit 41 provides patient 50 with stimuli, to which patient 50 responds by moving his eyes and/or his head. As previously discussed, the stimuli may comprise moving and/or alternating or flashing targets provided at display 54 that patient 50 follows with his eyes. The stimuli may also comprise instructions directing patient 50 to repeatedly move his head. Instructions directing patient 50 to move his head in certain ways may be displayed in written form as with a handout or pamphlet, on the patient's display 54 and/or output device 31 or as verbal instructions provided to patient 50 through headphone 56 or through a computer speaker. The eye movements and/or head movements of patient 50 are considered responses to the stimuli, and these responses are sensed and recorded by sensor apparatus 58 and, as the invention provides, converted and stored into the electronic document 60 of patient 50 as reaction data.

Because patient 50 responses to stimuli are stored into electronic document 60 as reaction data, they can be accessed by a doctor, a therapeutic specialist or other authorized clinical personnel for the purpose of evaluating and studying the responses. It should be understood that sensor apparatus 58 is configured and arranged to collect eye and head movement data and to convert them into reaction data. As previously mentioned, the reaction data are expressed as sensible indicia of the patient responses, namely, graphs, charts, numbers, figures, characters, etc. By having access to the stored responses, diagnoses and evaluations of the patient's dizziness or balance disorder can be made, which may be used for formulating adjustments to patient therapeutic and/or evaluative regimens as provided by patient curriculums. Consistent with this disclosure, any changes or modifications to patient curriculums are preferably introduced directly into patient electronic documents and then accessed and prosecuted by patients as provided herein. Alternatively, communications between clients 11A and 11B, including changes or modifications to therapeutic and/or evaluative curriculums, may be carried by conventional electronic mail.

The invention provides new and improved apparatus methods for treating and/or evaluating physical disorders or conditions, for recording measurable responses to stimuli, whether audible or visual stimuli and/or commands and/or instructions, and for prosecuting and managing therapeutic and/or evaluative regimens over a networked computer environment. The invention is not only useful in connection with dizziness and balance disorders, but may also be implemented for evaluating sight and visual acuity and hearing disorders or conditions, and stimuli may be appropriately formulated for eliciting patient responses in connection with evaluating sight, visual acuity and hearing conditions and disorders. Because the therapeutic and/or evaluative regimens are prosecuted and managed over a networked computer environment, patients are not inconvenienced with having to repeatedly travel to medical and/or therapeutic clinics during the course of home-based treatment and/or therapeutic regimens, and doctors and therapists and specialists are provided with a convenient means of providing and managing patient evaluative and/or therapeutic care.

Accordingly, the invention allows doctors, therapists, specialists and other authorized personnel to monitor patients on a continuing and ongoing basis during periods of home-based therapeutic and/or evaluative regimens, so that they can know whether their patients are diligently prosecuting their prescribed regimens and whether they are improving prior to subsequent follow-up examinations. As a result, many patients who are prescribed home-based exercises will improve at acceptable rates with the invention, which will, in many if not most instances, eliminate unnecessarily prolonged and expensive therapeutic treatment.

The invention has been described above with reference to one or more preferred embodiments. However, those skilled in the art will recognize that changes and modifications may be made in the described embodiments without departing from the nature and scope of the invention. Various changes and modifications to one or more of the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. A system comprising:
   a central client;
   a local client having stimuli delivery apparatus for providing stimuli designed to elicit eye and head movements and sensor apparatus for sensing the eye and head movements and recording the eye and head movements as reaction data; and
   a data structure accessible by the local client for storing the reaction data and by the central client for accessing and interacting with the reaction data.

2. The system of claim 1, wherein the data structure is accessible by at least one of the central and local clients over a publicly-accessible web site.

3. The system of claim 1, wherein the data structure is accessible by at least one of the central and local clients over a privately accessible web site.

4. The system of claim 1, wherein the data structure is accessible by the central and local clients over a localized computer network.

5. The system of claim 1, wherein the stimuli delivery apparatus and the sensor apparatus are carried by a head set unit.

6. The system of claim 1, wherein the stimuli comprises at least one of visual and audible stimuli.

7. A system comprising:
   networked central and local clients;
   each of the local clients having stimuli delivery apparatus for providing stimuli designed to elicit eye and head movements and sensor apparatus for sensing the eye and head movements and recording the eye and head movements as reaction data; and
   a data structure accessible by each of the local clients for storing the reaction data and by each of the central clients for accessing and interacting with the reaction data.

8. The system of claim 7, wherein the data structure is accessible by the central and local clients over a publicly-accessible web site.

9. The system of claim 7, wherein the data structure is accessible by the central and local clients over a privately accessible web site.

10. The system of claim 7, wherein the data structure is accessible by the central and local clients over a localized computer network.

11. The system of claim 7, wherein the stimuli delivery apparatus and the sensor apparatus of each of the local clients are carried by a head set unit.

12. The system of claim 7, wherein the stimuli comprises at least one of visual and audible stimuli.

13. A therapeutic treatment method comprising steps of:
    providing a central client and a remote local client each having electronic access to a data structure;
    at the local client, providing stimuli designed to elicit patient eye and head movements, collecting patient eye and head movements as patient reaction data in response thereto and storing the patient reaction data into the data structure; and
    at the central client, accessing the patient reaction data in the data structure.

14. The method of claim 13, wherein the step of providing stimuli further includes the step of providing exercise instructions.

15. The method of claim 13, wherein the step of providing stimuli further includes the step of providing visual stimuli.

16. The method of claim 13, wherein the step of providing stimuli further includes the step of providing audible stimuli.

17. A therapeutic treatment method comprising steps of:
    providing a central client and a remote local client each having electronic access to a data structure;
    at the central client, providing a patient with at least one of a therapeutic and evaluative program having stimuli designed to elicit patient eye and head movements;
    at the local client, implementing the stimuli and collecting patient eye and head movements as patient reaction data in response thereto and storing the patient reaction data into the data structure; and
    at the central client, accessing the patient reaction data in the data structure.

18. The method of claim 17, wherein the step of implementing the stimuli further includes the step of implementing exercise instructions.

19. The method of claim 17, wherein the step of implementing the stimuli further includes the step of implementing visual stimuli.

20. The method of claim 17, wherein the step of implementing the stimuli further includes the step of implementing audible stimuli.

* * * * *